(12) United States Patent
Frank et al.

(10) Patent No.: US 10,070,928 B2
(45) Date of Patent: Sep. 11, 2018

(54) IMPLANT PLACEMENT PLANNING

(71) Applicant: Mako Surgical Corp., Fort Lauderdale, FL (US)

(72) Inventors: Philip Harris Frank, Maplewood, NJ (US); Ali Zafar Abbasi, Davie, FL (US)

(73) Assignee: Mako Surgical Corp., Fort Lauderdale, FL (US)

( * ) Notice: Subject to any disclaimer, the term of this patent is extended or adjusted under 35 U.S.C. 154(b) by 323 days.

(21) Appl. No.: 14/789,462

(22) Filed: Jul. 1, 2015

(65) Prior Publication Data

US 2017/0000562 A1    Jan. 5, 2017

(51) Int. Cl.
| | |
|---|---|
| G09G 5/00 | (2006.01) |
| A61B 34/10 | (2016.01) |
| A61F 2/38 | (2006.01) |
| A61B 17/80 | (2006.01) |
| A61B 34/20 | (2016.01) |
| A61F 2/46 | (2006.01) |

(52) U.S. Cl.
CPC ............. *A61B 34/10* (2016.02); *A61B 17/80* (2013.01); *A61B 17/8061* (2013.01); *A61F 2/389* (2013.01); *A61B 34/20* (2016.02); *A61B 2034/102* (2016.02); *A61B 2034/105* (2016.02); *A61B 2034/107* (2016.02); *A61B 2034/108* (2016.02); *A61F 2002/3895* (2013.01); *A61F 2002/4633* (2013.01)

(58) Field of Classification Search
CPC ..... A61B 34/10; A61B 17/80; A61B 17/8061; A61B 2034/102; A61B 2034/105; A61B 2034/107; A61B 2034/108; A61B 34/20; A61F 2/389

USPC ................ 345/619, 629, 630, 632, 633, 634
See application file for complete search history.

(56) References Cited

U.S. PATENT DOCUMENTS

| | | | |
|---|---|---|---|
| 4,835,712 A | * | 5/1989 | Drebin .................... G06T 17/00 345/423 |
| 5,098,383 A | | 3/1992 | Hemmy et al. |
| 5,772,594 A | | 6/1998 | Barrick |
| 7,235,076 B2 | | 6/2007 | Pacheco |
| 7,725,162 B2 | | 5/2010 | Malackowski et al. |
| 8,014,848 B2 | | 9/2011 | Birkenbach et al. |

(Continued)

FOREIGN PATENT DOCUMENTS

WO    2013104682 A1    7/2013

OTHER PUBLICATIONS

Spine Navigation Brochure, Brainlab, pp. 1-19 (2013).

*Primary Examiner* — Xiao Wu
*Assistant Examiner* — Sarah Lhymn
(74) *Attorney, Agent, or Firm* — Lerner, David, Littenberg, Krumholz & Mentlik, LLP

(57) ABSTRACT

A method of planning a procedure to fasten an implant to a bone includes displaying a model of the bone and a model of the implant on a display device. The model implant is positioned on the model bone in a desired implant position. A first boundary volume of a first fastener configured to fasten the prosthesis to the bone is also displayed on the display device. The first boundary volume represents a range of possible positions that the first fastener may have with respect to the prosthesis when fastened to the bone. The boundary volume may be used to determine a desired size, shape, and/or positioning of the fastener with respect to the bone.

20 Claims, 11 Drawing Sheets

(56) References Cited

U.S. PATENT DOCUMENTS

| | | |
|---|---|---|
| 8,055,487 B2 | 11/2011 | James |
| 8,116,847 B2 | 2/2012 | Gattani et al. |
| 8,241,292 B2 | 8/2012 | Collazo |
| 8,484,001 B2 | 7/2013 | Glozman et al. |
| 8,838,205 B2 | 9/2014 | Shoham et al. |
| 9,011,444 B2 | 4/2015 | Primiano et al. |
| 2005/0101970 A1 | 5/2005 | Rosenberg |
| 2005/0119561 A1* | 6/2005 | Kienzle, III ........ A61B 17/1703 600/425 |
| 2006/0195198 A1* | 8/2006 | James .................... A61B 90/36 700/1 |
| 2008/0281330 A1* | 11/2008 | Ferrante ............. A61B 17/1703 606/96 |
| 2009/0018560 A1* | 1/2009 | Mayer ................. A61F 2/30721 606/151 |
| 2009/0143788 A1 | 6/2009 | Fang et al. |
| 2010/0217336 A1 | 8/2010 | Crawford et al. |
| 2012/0109137 A1 | 5/2012 | Iannotti et al. |
| 2012/0130686 A1 | 5/2012 | Graumann |
| 2013/0060146 A1 | 3/2013 | Yang et al. |
| 2014/0277548 A1 | 9/2014 | Cohen et al. |
| 2014/0277567 A1 | 9/2014 | Collazo et al. |
| 2014/0357985 A1 | 12/2014 | Cardelino et al. |

\* cited by examiner

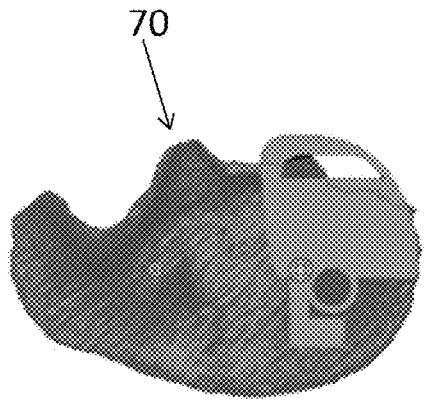
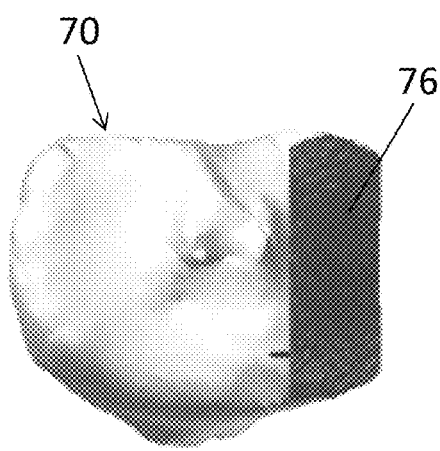
FIG. 5A  FIG. 5B
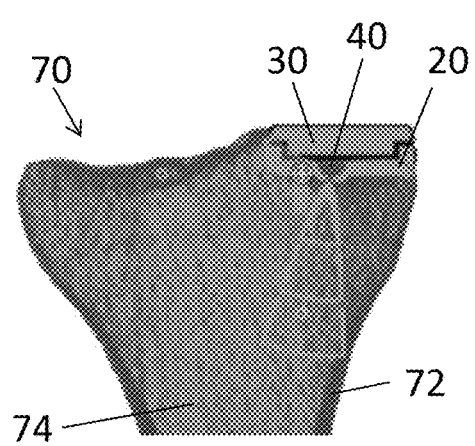
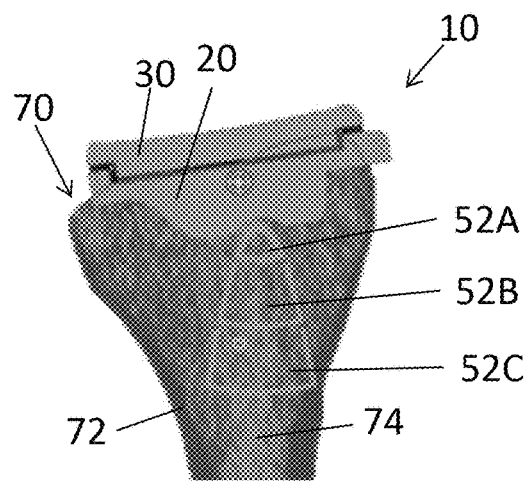
FIG. 5C  FIG. 5D

IMPLANT PLACEMENT PLANNING

BACKGROUND

The present disclosure relates generally to orthopedic prostheses. In particular, the present disclosure relates to planning the size, shape, position, and/or orientation of an implant relative to a patient's anatomy or another implant.

Orthopedic knee implant systems have been used for many years to treat patients with knee joints that have been damaged by trauma or disease, such as osteoarthritis, rheumatoid arthritis, and avascular neurosis. A knee arthroplasty procedure generally involves resecting, cutting, or resurfacing the damaged sections of the knee and replacing them with an endoprosthesis or implant.

Most knee implant systems are tricompartmental or total implants and the surgical procedure used with such implants is commonly known as total knee arthroplasty. These implants are known as tricompartmental implants because they are used when the knee joint is prepared to receive an implant by resurfacing or resecting the three articulating compartments, i.e., the medial and lateral femorotibial and the patellofemoral surfaces. Regardless of the type of implant used, arthroplasties generally require the bone to be specifically prepared to receive a corresponding implant by resecting, cutting, resurfacing, or otherwise deforming the bone to accept the implant.

Unicondylar or unicompartmental knee implants have become of great interest in the orthopedic industry due to their less invasive nature while providing the option of maintaining healthy knee compartments if present in the knee joint. Unicondylar knees typically resurface or resect the medial or lateral femorotibial articulating surfaces thus allowing preservation of the other compartments not suffering from damage due to trauma or disease.

Historically, orthopedic devices have been mated with host bone by cementing them in place using methyl methacrylate, generally termed bone cement. The use of bone cement in attaching a prosthesis within or onto a prepared bone provides an excellent immediate fixation but has various disadvantages that may appear over time. Physical loads are repeatedly applied to the implant over its life. If bone cement is used to secure a unicompartmental knee prosthesis, the bone cement may fatigue and fracture under the repeated loading. In some instances, degradation of the bone cement integrity may cause the device to become loose, thereby necessitating replacement. Old bone cement must be removed from the host bone as part of the implant replacement procedure. This procedure can be complex, time consuming and potentially destructive to healthy bone structures surrounding the implant. Furthermore, conventional bone cement is cured after it has been dispensed into the patient's joint. Loose undetected cement fragments can remain in the joint space and, with patient mobility over time, increase the degradation rate of articulating implant surfaces.

More recently, the development of orthopedic implant designs has moved towards satisfying the requirements of high demand patients. Patients today require more from their implants, and because patients are living longer, they require implants that to last longer. Accordingly, developments have been made in materials used to make orthopedic implants to improve implant longevity, such as highly porous metals that improve biological bone fixation. These implants are generally termed press-fit or cementless.

Recognizing the disadvantages of cement fixation techniques, prior art devices have also been developed that utilize other mechanical attachment means to join an implant to bone for immediate stabilization. Although various implant surface treatments intended to bond with bone biologically for long term stable attachment have proven successful, an initial fixation and stabilization is required before the bone growth can occur. One technique of mechanically securing an implant is to affix it to the bone with screws, or other mechanical fasteners. However, due to the nature of the bone surrounding the surgical site, and other limiting factors such as artery location and the like, it is desirable to insert the screw(s) into the bone with optimal trajectories.

BRIEF SUMMARY OF THE INVENTION

According to one aspect of the disclosure, a method of planning a procedure to fasten an implant to a bone comprising includes displaying on a display device a model of the bone. A model of the implant is also displayed on the display device. The model implant is positioned on the model bone in a desired implant position. A first boundary volume of a first fastener configured to fasten the prosthesis to the bone is displayed on the display device. The first boundary volume represents a range of possible positions that the first fastener may have with respect to the prosthesis when fastened to the bone. The first boundary volume may have a plurality of volume portions such that each volume portion represents possible positions of a different sized first fastener. A first fastener size that has a boundary volume positioned entirely within the model bone may also be provided. The step of displaying the model bone may include displaying bone quality information, such as bone density, on the model bone.

A second boundary volume representing a second range of possible positions of a second fastener configured to couple the prosthesis to the bone may also be displayed on the display device. An overlap volume defined by volume occupied by both the first and second boundary volumes may be indicated on the display.

According to a further aspect of the disclosure, a method of planning a procedure to fasten an implant to a bone includes displaying on a display device a model of the bone and a model of the implant having at least one aperture for receiving a fastener. The model implant is positioned on the model bone in a desired implant position. A first boundary volume of a first fastener configured to fasten the prosthesis to the bone is also displayed on the display device. The first boundary volume represents a range of possible positions that the first fastener may have when fully received within the at least one aperture. The first boundary volume may have a plurality of volume portions such that each volume portion represents possible positions of a different sized first fastener. A first fastener size that has a boundary volume positioned entirely within the model bone may be provided. The step of displaying the model bone may include displaying bone quality information, such as bone density, on the model bone. A second boundary volume representing a second range of possible positions of a second fastener configured to couple the prosthesis to the bone may also be displayed. An overlap volume defined by volume occupied by both the first and second boundary volumes may be indicated on the display. The prosthesis may be a tibial implant or a bone plate According to yet another aspect of the disclosure, a computer system includes at least one processor configured to execute instructions to display a model of a bone and a model of an implant on a display device, and to change a position of the model implant on the model bone to a desired implant position in response to user input. The processor may also be configured to display on the display device a first boundary volume of a first fastener configured to fasten the implant to the bone, the first boundary volume representing a range of possible positions that the first fastener may have with respect to the prosthesis when fastened to the bone.

BRIEF DESCRIPTION OF THE DRAWINGS

FIGS. 5A-D show different views of a model tibia implants overlaid on a model tibia.

DETAILED DESCRIPTION

Figure 1A:
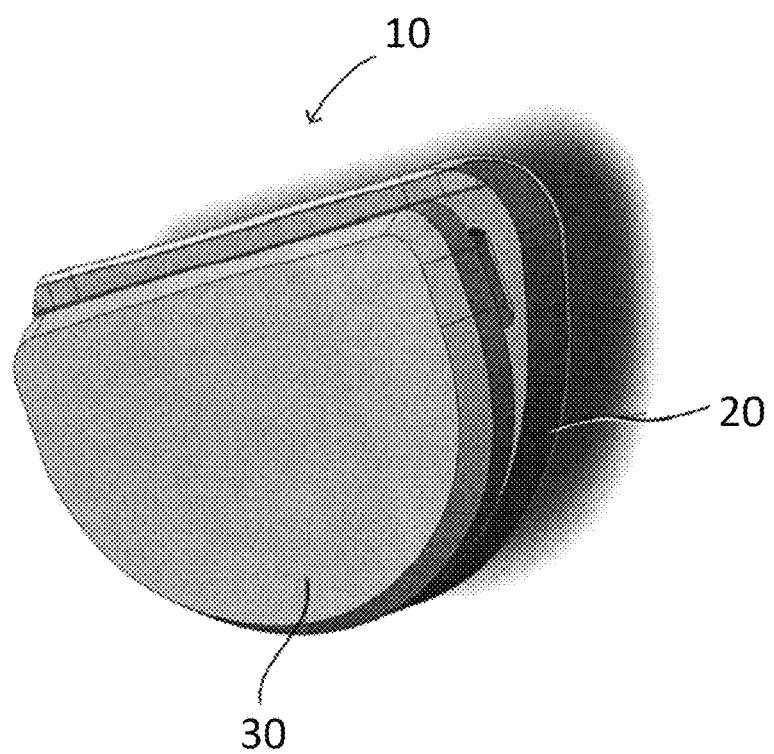
FIG. 1A is a top perspective view of a unicondylar tibial implant assembly.
Figure 1B:
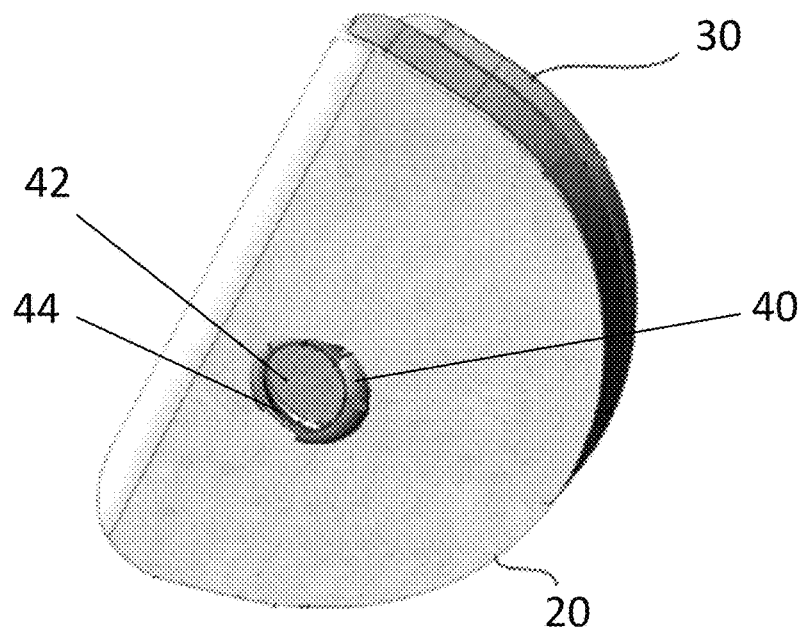
FIG. 1B is a bottom perspective view of the unicondylar tibial implant of FIG. 1.

When referring to specific directions in the following discussion of certain implantable devices, it should be understood that such directions are described with regard to the implantable device's orientation and position during exemplary application to the human body. Thus, as used herein, the term "proximal" means closer to the heart and the term "distal" means more distant from the heart. The term "inferior" means toward the feet and the term "superior" means toward the head. The term "anterior" means toward the front of the body or the face and the term "posterior" means toward the back of the body. The term "medial" means toward the midline of the body and the term "lateral" means away from the midline of the body. Also, as used herein, the terms "about," "generally," and "substantially" are intended to mean that slight deviations from absolute are included within the scope of the term so modified. Likewise, for purposes of convenience and clarity only, directional terms such as top, bottom, above, below and diagonal, may be used with respect to the accompanying drawings. Such directional terms used in conjunction with the following description of the drawings should not be construed to limit the scope of the invention in any manner not explicitly set forth. Additionally, the term "a," as used in the specification, means "at least one." The terminology includes the words above specifically mentioned, derivatives thereof, and words of similar import.

Although much of the disclosure below is directed to screw length and/or trajectory planning in connection with a unicondylar knee implant, it should be understood that the implant size, shape, position, and/or orientation planning methods disclosed herein may be applicable to any surgical procedure in which an implant, such as a screw (or pin, or like device) is to be implanted into a patient relative to another implant or a patient's anatomy, such as a bone, including in connection with other bone implants, such as bone plates or joint implants, including other knee implants and implants for other joints, such as ankle, shoulder and hip implants, for example. It should further be understood that the term trajectory, as used herein, may generally refer to the three-dimensional position and/or orientation of an object, such as a screw, in space.

As noted above, partial knee implants, also known as unicondylar or unicompartmental knee implants, are designed to replace either a medial or lateral compartment of a knee joint. A unicondylar replacement assembly may include a tibial implant, either by itself or in conjunction with an implant designed to replace a femoral condyle. The preparation of the bone to accept such implants may be facilitated by instrumentation such as bone files, burrs, saws, punches, computer and/or robot assisted instrumentation/ navigation systems. Once the bone is prepared, the implant may be secured to the bone by different means, including bone cement which bonds to the implant and impregnates the bone resulting in fixation of the implant to the bone interface.

The present disclosure relates, at least in part, to methods and devices for facilitating fixation directly to the bone, i.e., without bone cement. Such fixation without bone cement is referred to herein as cementless fixation. The present disclosure addresses, among other issues, the facilitation of planning and carrying out the fixation of an implant directly to bone with one or more screws or related fasteners, such as bone pins. It should also be noted that although the description focuses on cementless fixation, the concepts described herein may be used with bone cement, although it may not be necessary.

As noted above, the present disclosure relates to the planning of the size, shape, position, and/or orientation of an implant to be implanted into a patient relative to a patient's anatomy, such as a bone, and/or relative to another implant. A first example of such planning is described in relation to a partial knee arthroplasty ("PKA") procedure, although other procedures employing the inventive methods are described in more detail below. FIGS. 1A-D illustrate an embodiment of a unicondylar tibial implant 10 that may be fixed to a bone pursuant to the concepts disclosed herein. Tibial implant 10 may generally include a tibial tray or baseplate 20 and a bearing surface or member 30. Of course, as noted above, although the concepts are described herein in connection with a unicondylar implant for the tibia, the disclosure has applicability to other types of implants. The tibial implant 10 can be constructed from any combination of solid metal, porous metal, polymers and/or other resorbable materials. For instance, it is contemplated to form the bearing 30 of a polymer material such as PEEK, and the baseplate 20 of a metal such as titanium or stainless steel. Likewise, it is contemplated to form baseplate 20 of different materials, e.g., a porous portion of baseplate 20 may be formed of a different material than the remainder of the implant.

For purposes of convenience only, and not by way of limitation, the foregoing description of unicondylar tibial implant 10 will be described and illustrated with respect to a unicondylar tibial implant 10 for a medial tibial condyle. However, the foregoing description and features of the unicondylar tibial implant 10 are equally applicable to a unicondylar tibial implant for a lateral condyle, such similar features of the lateral unicondylar tibial implant being substantially mirror images of such features of the medial unicondylar tibial implant. Of course, it is also contemplated that the medial and lateral versions of the assembly may be of a different construction to accommodate the different bony anatomy of the medial and lateral portions of the tibia.

Figure 2A:
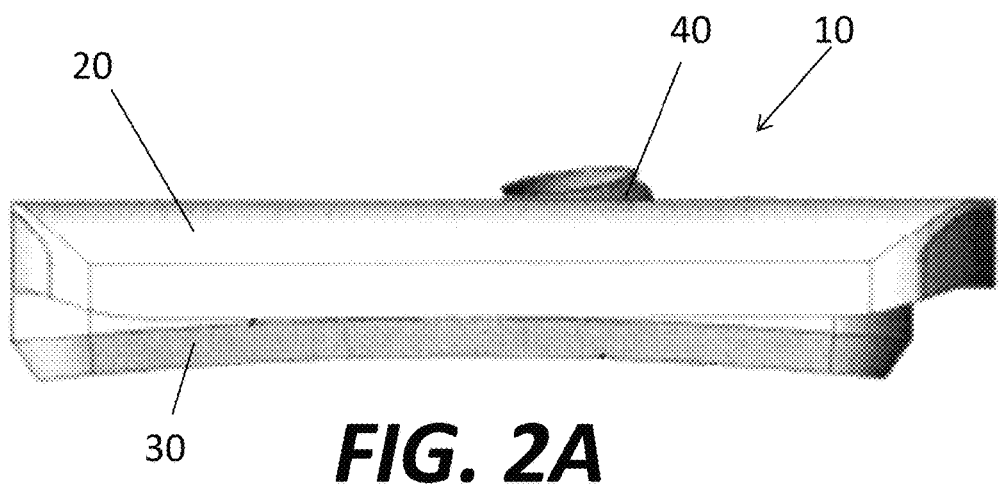
FIG. 2A is a side view of the unicondylar tibial implant of FIG. 1.
Figure 2B:
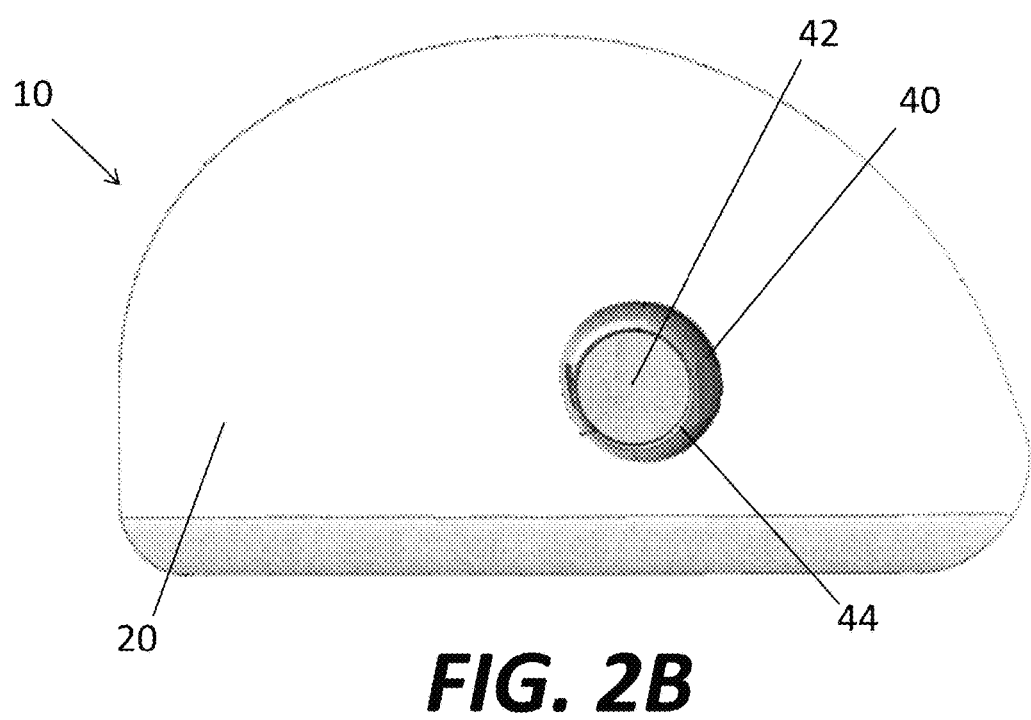
FIG. 2B is a bottom view of the unicondylar tibial implant of FIG. 1.

The tibial implant 10 may be provided with a through-hole or aperture 40 through which another device, instrument or material e.g., a locking or non-locking bone screw 50 (as is shown in FIGS. 2A and 2B) can be inserted. The aperture 40 may be shaped and sized for the passage of the bone screw 50 through a superior aspect of the tibial implant 10 into the bone beneath the underside or inferior surface of the baseplate 20. The aperture 40 may be fully or partially threaded or may not be threaded. Aperture 40 may be designed with a ramp surface (not shown) such that the aperture may form a compression hole or may be designed such that the bone screw 50 can be angulated with respect to one or both of the top surface 20a and bottom surface 20b of baseplate 20 to achieve a desired direction by the user. Such apertures 40 and bone screws 50 are readily known in the art and a detailed description of their structure and operation is not necessary for a complete understanding of the present invention. It should further be noted that, although it is preferable to employ a separate bearing surface 30 on top of baseplate 20, for example to cover aperture 40 and a screw 50 seated therein, it is not necessary to employ a bearing surface 30 separate from baseplate 20.

The tibial implant 10 may employ the use of a knockout plug 42 formed within the aperture 40 and out of a material that is metallurgically continuous with the greater bulk of the tibial implant 10. The knockout plug 42 may be configured to be removed from the remainder of the tibial implant 10 via a boundary shear section or weakened area 44 around the plug 42 (see FIG. 2B) upon the application of a suitable force. The plug 42 may be machined into the baseplate 20 or built in final form through an additive manufacturing process such as by direct metal laser sintering, for example. The aperture 40 may be obstructed by the knockout plug 42 so that the superior surface of the baseplate facing the bearing component 30 is fully continuous without any path through which debris or material could pass through the baseplate 20 to the bone engaging underside of the tibial implant 10. Thus, in the event of backside wear of the bearing component 30, wear particles are less likely to migrate out of the baseplate 20 than if an already present aperture were in place. The knockout plug 42 can optionally include a threaded stud (not illustrated), which mates to instrumentation to facilitate removal of the knockout plug 42.

In sum, the baseplate 20 has an initially covered aperture 40 into which a screw 50 can be placed to stabilize the tibial implant 10 to the prepared bone upon implantation. Other unicondylar tibial implants are described in greater detail in U.S. Patent Publication No. 2014/0277548, the disclosure of which is hereby incorporated by reference herein.

Figure 3A:
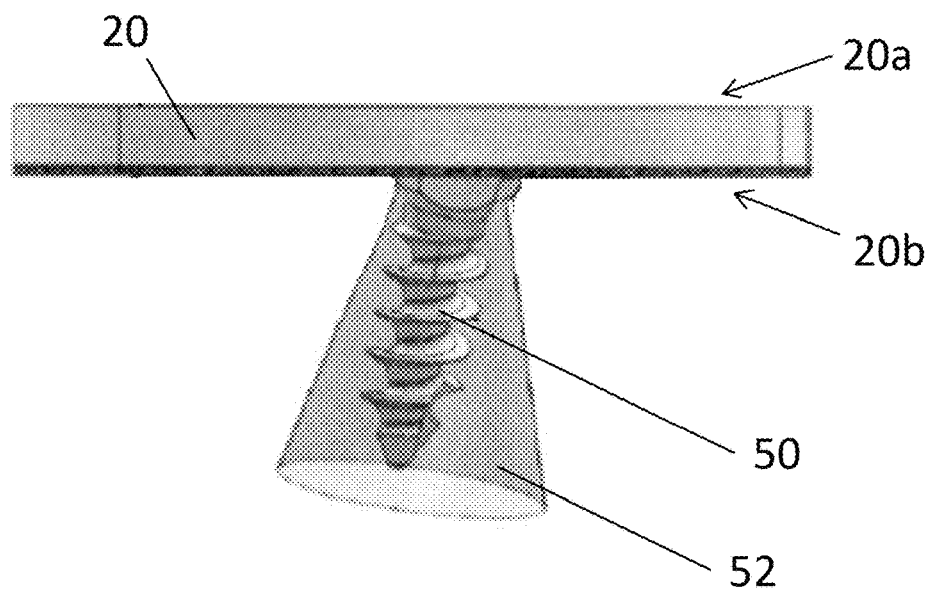
FIG. 3A is a side view of the unicondylar tibial implant of FIG. 1 with a bone screw positioned within a through hole of the tibial implant.
Figure 3B:
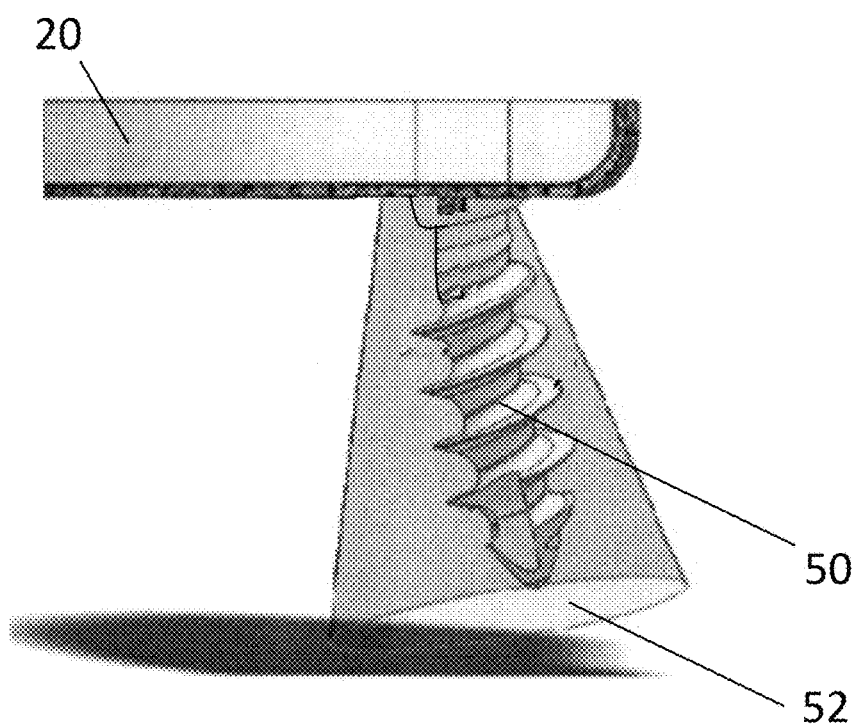
FIG. 3B is a rear view of the assembly of FIG. 3A.

The aperture 40 of baseplate 20 may have a contoured shape. For example, the aperture 40 may take the form of a portion of a sphere or another rounded surface. Similarly, screw 50 may have a contoured head, such as a spherical or partially spherical head. Based on the particular shapes of the aperture 40 and the head of the screw 50, the screw 50 may have a range of possible angulation with respect to the tibial implant 10. For example, as shown in FIGS. 3A-B, the shaft of screw 50 may have a range of possible positions described by a volume generally in the shape of a cone 52 (or a portion thereof).

It may be preferable to preoperatively plan the placement of screw 50 with respect to the bone into which the screw will be inserted during an implantation procedure. For example, through preoperative or even intraoperative planning, a surgeon may determine that a particular size screw 50 and/or particular angulation of the screw 50 is undesirable, for example because such positioning may result in a portion of the screw 50 being positioned too close to the cortical wall or shell of a bone, or even penetrating beyond the cortical shell of the bone. A variety of additional variables and methods may be used to preoperatively or intraoperatively plan a desired length and/or trajectory of one or more screws relative to an implant and bone to which the implant is to be secured, for example including the tibial implant 10 system described above. For example, the position of aperture 40 with respect to baseplate 20 and the position of baseplate 20 with respect to a bone 70 may also be used to preoperatively or intraoperatively plan a desired length and/or trajectory of one or more screws. Other variables such as bone quality, patient morphology and kinematics, for example, may also be used in screw planning.

Although much of the disclosure is generally described in relation to the use of tibial implant 10 on a patient's tibia, it should be clear that the concepts described herein may apply with equal force to other bone implants secured to bone with a bone screw or other fastener, such as acetabular cups of hip implants, or bone plates fastened to a long bone.

Figure 4:
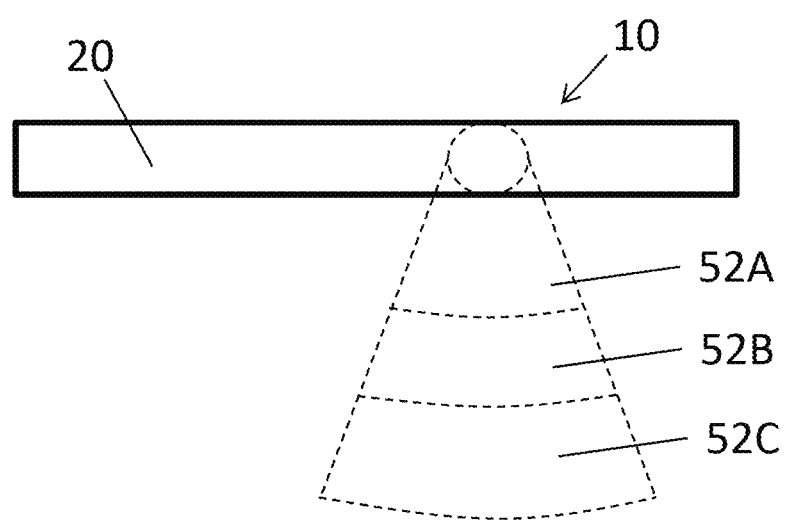
FIG. 4 is a schematic side view of the tibial implant assembly of FIG. 1 with ranges of potential screw volume occupancies illustrated.

For a particular type of screw 50 and tibial implant 10, a number of variables may determine the entire volume which the screw 50 may potentially occupy. For example, FIG. 4 provides a simplified representation tibial implant 10 and volumes that may be occupied by different screws. For example, the entire volume that may be potentially occupied by a screw 50 assembled to the baseplate 20 of tibial implant 10 may be determined by two factors: (1) the length of the shaft of screw 50; and (2) the shape of the head of screw 50 and the corresponding shape of the aperture 40 of the baseplate 20. In other words, the length of screw 50 and potential angulation of screw 50 with respect to baseplate 20 may define a particular volume that may be occupied by screw 50, whereas the position of that particular volume with respect to the bone may be determined by the placement of baseplate 20 with respect to the bone and the position of aperture 40 with respect to baseplate 20. Based on these or other factors, a preoperative plan, which may for example be displayed on a computer display or other visual medium, a representation of tibial implant 10 and the volume that a variety of screws of different sizes may occupy may be simultaneously displayed. For example, FIG. 4 shows the tibial implant 10, a first volume 52A that a relatively short screw may occupy, a second volume 52B (which includes volume 52A) that a screw of medium length may occupy, and a third volume 52C (which includes volumes 52A and 52B) that a relatively long screw may occupy. Volume 52A may define a cone of volume that could be occupied by a 15 mm screw, while volume 52B defines a cone of volume that could be occupied by a 25 mm screw, and volume 52C defines a cone of volume that could be occupied by a 35 mm screw. It should be understood that these three sizes of screws are merely provided as examples. In addition, other types of implant and/or screw shapes may be taken into account. Similarly, although the term "cone" is generally used in relation to the volume that the screw may occupy, the volume is more precisely frustoconical, although the volume need not meet the precise mathematical definition of a cone or frustocone, and the precise shape of the volume depends on the characteristics of screw 50 and the aperture 40. Further, it should be noted that the volumes displayed preferably represent positions of screw 50 when the screw is an in implanted position, for example when the head of the screw is fully seated into the aperture 40 of the baseplate 20 or when the screw 50 is otherwise fully received in the aperture 40.

The representation of the tibial implant 10 and the volumes 52A-C that may be occupied by the screw 50 may be overlaid on a graphical representation of the tibia 70 to which the tibial implant 10 will be secured. For example, as shown in FIGS. 5A-D, a computer monitor or other visual medium may display tibia 70 in different views, for example a transverse view (FIG. 5A), a perspective view (FIG. 5B), a coronal view (FIG. 5C), and a sagittal view (FIG. 5D). These views may be displayed separately or together in any combination. Each view of the tibia 70 may be based on data obtained from medical imaging, for example an X-Ray or CT scan. In particular, it is preferable that the medical imaging data includes physiological information of the tibia 70, such as absolute or relative bone density information. For example, as best seen in FIGS. 5C-D, tibia 70 may be displayed with a range of shading or color, such that a relative high-density portion of the tibia 70, such as the cortical shell 72, is discernable from a relative low-density portion of the tibia 70, such as the cancellous core 74. By overlaying a graphical representation of the tibial implant 10 on a graphical representation of the tibia 70, a surgeon may be able to determine whether certain sizes and/or positions of screw 50 may be unacceptable, for example because the screw 50 would be positioned too close to the cortical shell 72. For example, a screw 50 coupling the baseplate 20 to the tibia 70 preferably does not exit the bone at any point.

Figure 6:
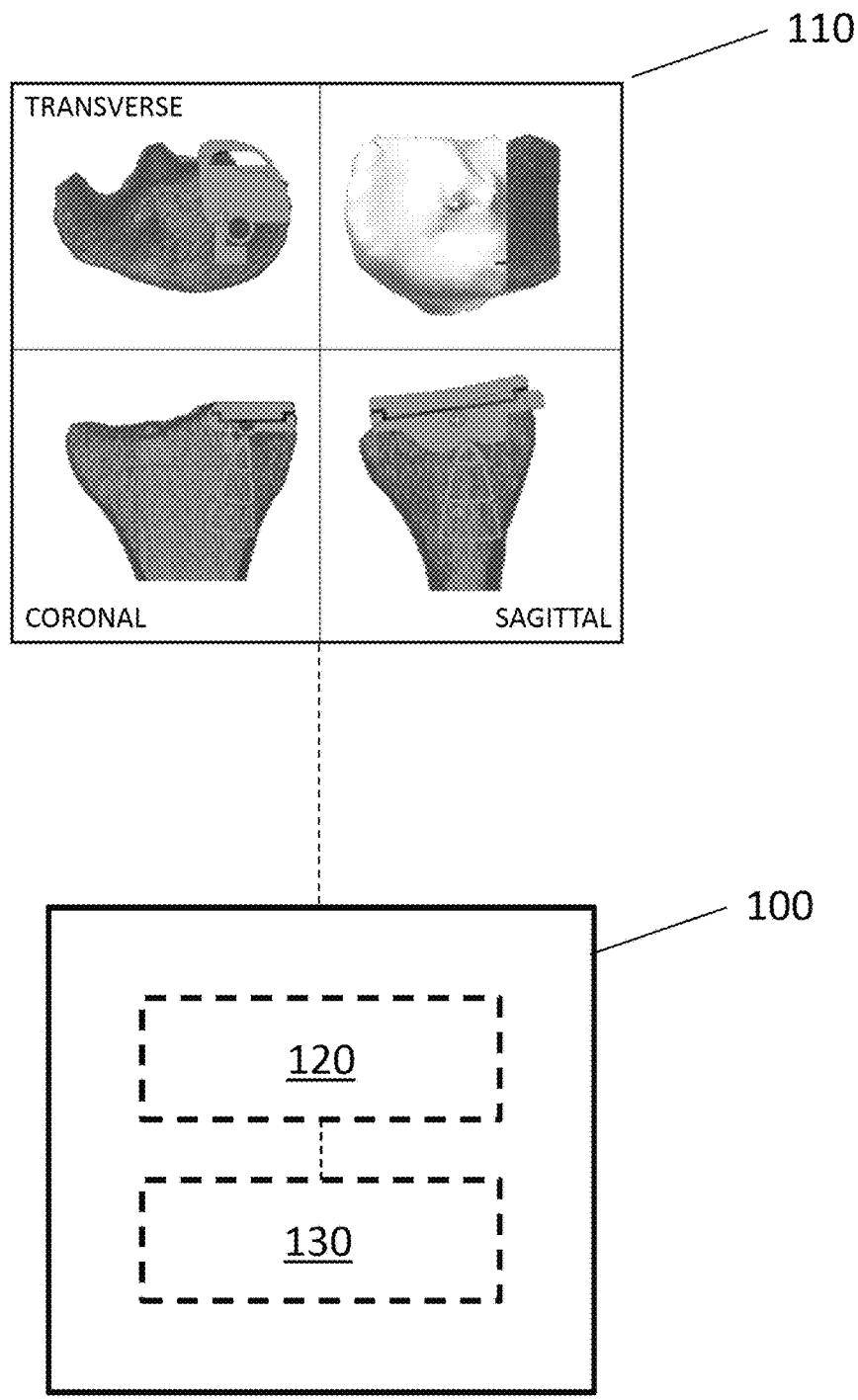
FIG. 6 is a schematic representation of a pre-operative planning system.

In an exemplary surgical procedure employing the concepts disclosed herein, a patient that has been determined to require a unicondylar tibial implant 10 undergoes medical imaging, for example, a CT or MRI scan. Data from the medical imaging may be used to create a model of the bone if desired. As shown in FIG. 6, one or more views of a graphical representation of the tibia 70 are displayed on a visual medium, such as a computer monitor 110, for the surgeon to review. The surgeon may simulate a planned bone resection 76, for example as shown in FIG. 5B. In a unicondylar tibial implantation procedure, the planned bone resection may be a proximal substantially planar resection 76 of the medial or lateral condyle. Viewing the tibial bone that will remain after the planned resection 76 is made may assist the surgeon in determining the quality of the bone with which the baseplate 20 and screw 50 will interact.

With the graphical representation of the tibia 70 displayed on monitor 110, the surgeon may select a model of the tibial implant 10. For example, one or more models of tibial implants may be stored in the memory 120 of a computer 100 in communication with the monitor 110. The memory 120 may include, for example, standard or non-standard sizes of available medial or lateral tibial implants 10. The surgeon selects the desired tibial implant 10, and, with the aid of processor 130, a model of the tibial implant 10 may be displayed on monitor 110 and overlaid on the graphical representation of the tibia 70. The surgeon may translate and/or rotate the model of the tibial implant 10 to a desired operative position on the graphical representation of the tibia 70. Each model tibial implant 10 may include a combination of model volumes which correspond to volumes that may be occupied by one or more sizes of screws 50 for use in securing the baseplate 20 to the tibia 70. For example, as shown in FIGS. 5C-D, the model of the tibial implant 10 may include representations of volumes 52A-C corresponding respectively to the volume that may be occupied by screws 50 having lengths of 15 mm, 25 mm, and 35 mm.

As the surgeon translates and/or rotates the model of the tibial implant 10 through a variety of positions, the volumes 52A-C move correspondingly to show the surgeon the entire range of possible positions that a screw 50 securing the baseplate 20 to the tibia 70 may occupy. Viewing the position of the model tibial implant 10 and possible positions of a variety of screws 50 with respect to the geometry of tibia 70, as well as physiological bone properties illustrated in the model tibia 70, the surgeon may choose the optimum or desired combination of placement of tibial implant 10 on tibia 70, as well as size, shape, and orientation of screw 50 to secure the baseplate 20 to the tibia. For example, for a given position of tibial implant 10, the surgeon may determine a desired length and orientation of screw 50 to ensure the planning of the screw 50 maintains a desired distance from the cortical shell 72 and is also positioned, for example, in bone having good quality, as determined by the bone density mapped onto the representation of tibia 70.

Although the above described procedure may be performed pre-operatively or intra-operatively, it is preferable for the planning to occur pre-operatively. Once the surgeon has determined the desired placement of tibial implant 10 and position and size/shape of screw 50, the surgeon may begin the procedure. The surgeon may utilize navigation systems to facilitate the procedure. Surgical navigation systems are described in greater detail, for example, in U.S. Pat. No. 7,725,162, the contents of which are hereby incorporated by reference herein. In one example, a registration tool may be used to register landmarks of the patient's tibia to a navigation system, and trackers may be provided on the tibia and/or tools used in the procedure so that a computer monitor or other display device can display in real-time or near real-time the position of the tibia 70 and the position of surgical tools as they move in relation to the tibia 70. The navigation system may be combined with the screw trajectory planning to help ensure that the screw 50 is implanted in a desired position, as described in greater detail below.

Figure 7A:
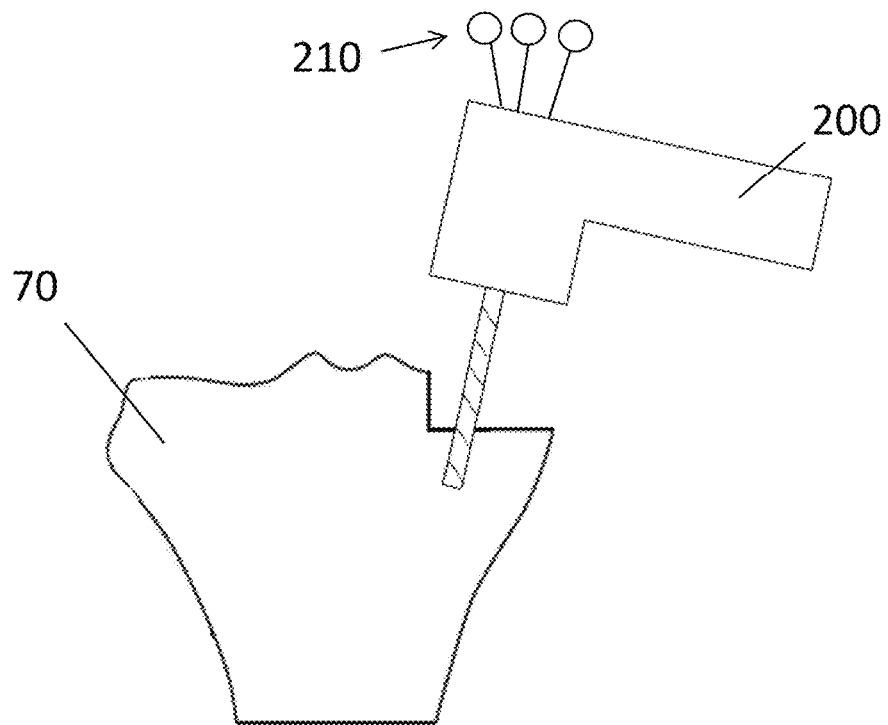
FIG. 7A is a highly schematic view of an operative step of drilling into the tibia.
Figure 7B:
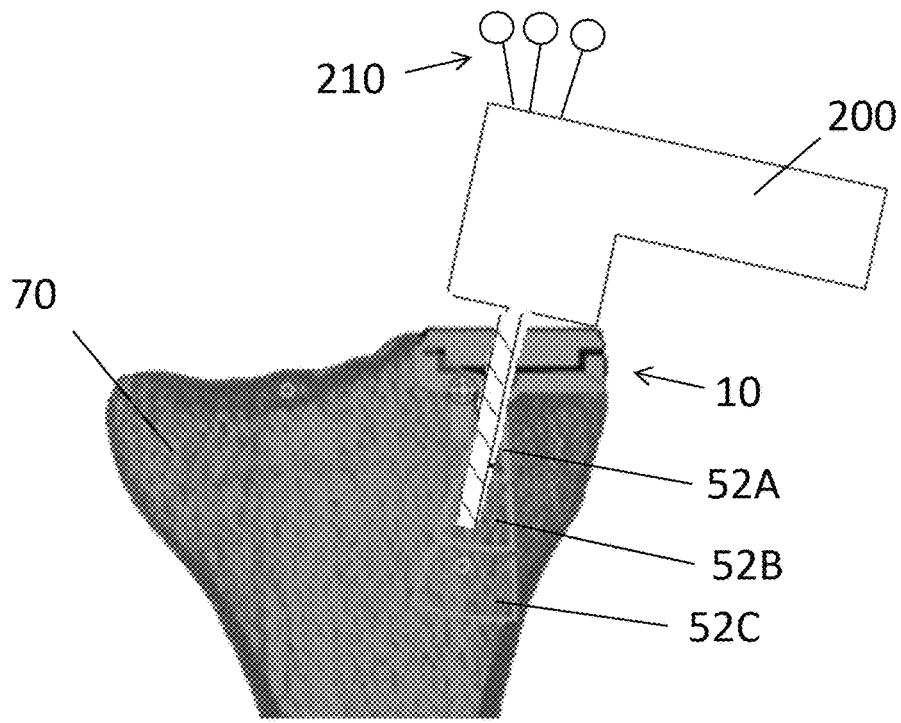
FIG. 7B is a highly schematic view of a navigation system illustrating the procedure of FIG. 7A.

Once registered, tibia 70 in the operating room (shown in FIG. 7A) may be simultaneously represented on a graphical display (shown in FIG. 7B). The graphical representation of tibia 70 may be the same as that chosen by the surgeon during the pre-operative planning, for example as shown in FIG. 5C. Thus, the representation of the tibia 70 used during navigation may include the model tibial implant 10 and one or more volumes 52A-C that screw 50 may occupy. When drilling a pilot hole into the tibia 70 for screw 50 (or otherwise directly drilling screw 50 into the tibia 70 without a pilot hole), a drill 200 may be used by the surgeon. The drill 200 may be registered to the navigation system, for example by trackers 210. Thus, as the drill 200 is driven into the tibia 70 (shown in FIG. 7A, a representation of the drill 200 and its position relative to the tibia 70 is provided on the navigation system (shown in FIG. 7B). With this feature, the surgeon is able to confirm in real time that the drill 200 and/or the screw 50 being inserted into tibia 70 is positioned mostly or entirely within the appropriate volume 52A-C chosen during pre-operative planning.

During the implant procedure, portions of one or more volumes 52A-C may be provided with further indicia to aid the surgical procedure. For example, a highly desirable volume within the volumes 52A-C may be color coded green, a less desirable volume within the volumes 52A-C may be color coded yellow, and a least desirable volume within the volumes 52A-C may be color coded red. With this feature, the surgeon may be provided with further guidance to help increase the accuracy with which the surgeon is able to place the screw 50 into the desired volume of bone. It should be understood that the color coding system provided above is merely an example, and other indicia may be used.

Although the tibial implantation procedure above is described as a manual procedure utilizing the pre-operative planning, the concepts described herein are not so limited. For example, the position of the tibial implant 10 chosen pre-operatively, as well as the desired position of a particular screw 50, may be input into the navigation system as described above, with the navigation system operably coupled with a partially or fully automated surgical system. For example, the navigation system may be coupled to a robotic arm with a drill attachment. The robotic arm may utilized the preoperative data to drill screw 50 into tibia 70, with the drilling confined to the appropriate volume 52A-C chosen during preoperative planning. Alternately, the robot may be partially automated. For example, the data for volume 52A-C may be utilized to provide boundaries for a drill, for example attached to a robotic arm, with the robotic arm and drill being manually controlled by the surgeon. As the surgeon uses the robotic arm and drill attachment to drill the pilot hole (or to directly drill the screw 50 into the tibia 70), the surgeon may move the drill within the pre-defined volume 52A-C, with the robot inhibiting movement of the drill outside that pre-defined volume. Effectively, this partially automated system allows the surgeon full manual control of drilling within the pre-defined volume 52A-C, and eliminates the ability of the surgeon to drill outside the pre-defined volume 52A-C.

Figure 8A:
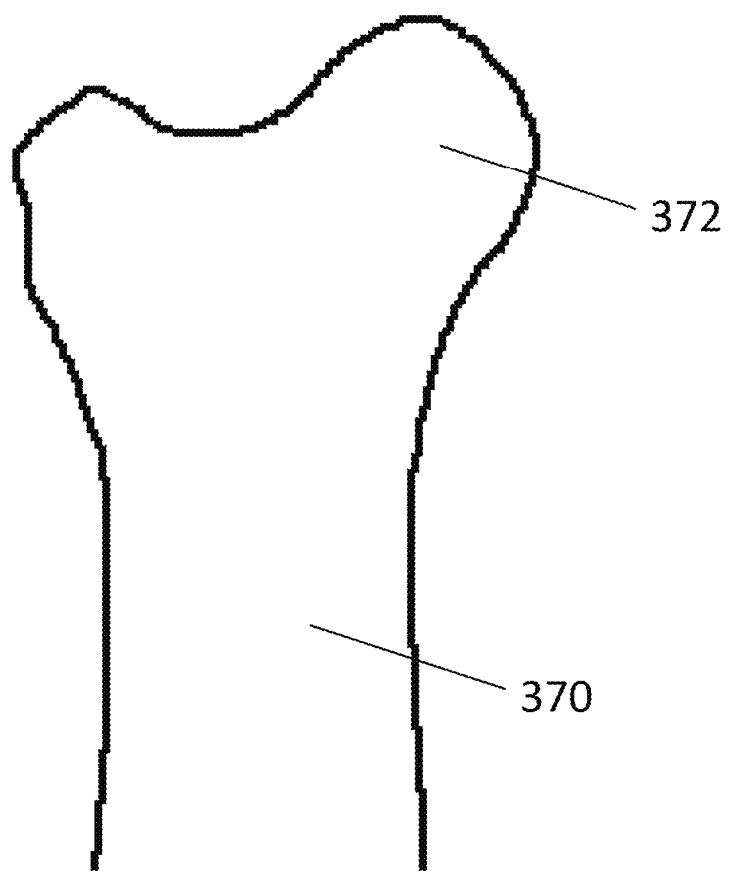
FIG. 8A is a highly schematic view of a proximal humerus.
Figure 8B:
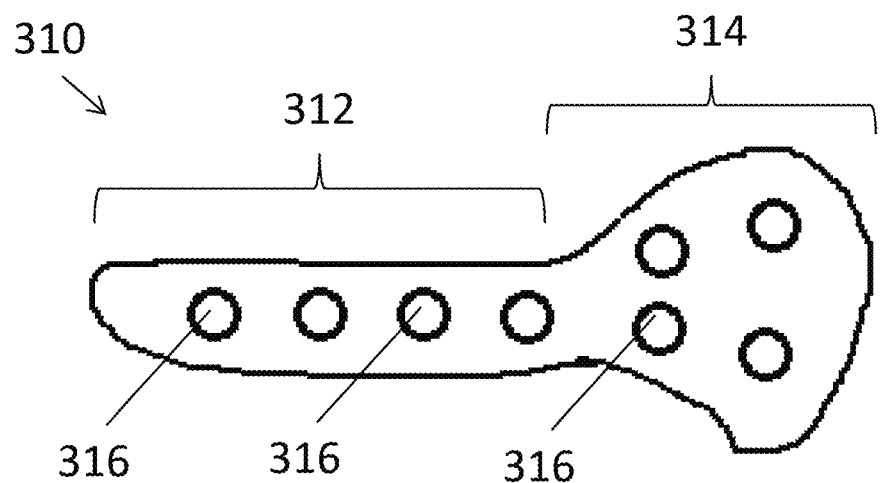
FIG. 8B is a highly schematic view of a bone plate.

One embodiment of the inventive method has been described above in relation to screw size, shape, position, and/or orientation planning with respect to the implantation of a unicondylar tibial implant system 10 onto a bone using a single screw 50. However, as noted above, the planning methods are not so limited. For example, the planning methods may be used in planning and/or carrying out the implantation of a bone plate 310 onto a long bone, such as the humerus 370. As shown in FIG. 8A, the humerus 370 is a long bone of the arm with a head 372 that articulates in the glenoid cavity of the scapula. When the head 372 of the humerus 370 breaks, one method of treatment may be fixing a bone plate 310 to the head 372 and along the shaft of the humerus 370. As shown in FIG. 8B, bone plate 310 may include a first, relatively straight narrow shaft portion 312 and a larger, rounded head portion 314 angled with respect to the shaft portion 312. The shaft portion 312 of bone plate 310 may be configured for coupling to the shaft of the humerus 370, with the head portion 314 configured for coupling to the head 372 of the humerus 370. A number of apertures 316 may be positioned along the bone plate 310, the apertures 316 configured to receive bone screws or pegs to couple the bone plate 310 to the humerus 315.

Figure 8C:
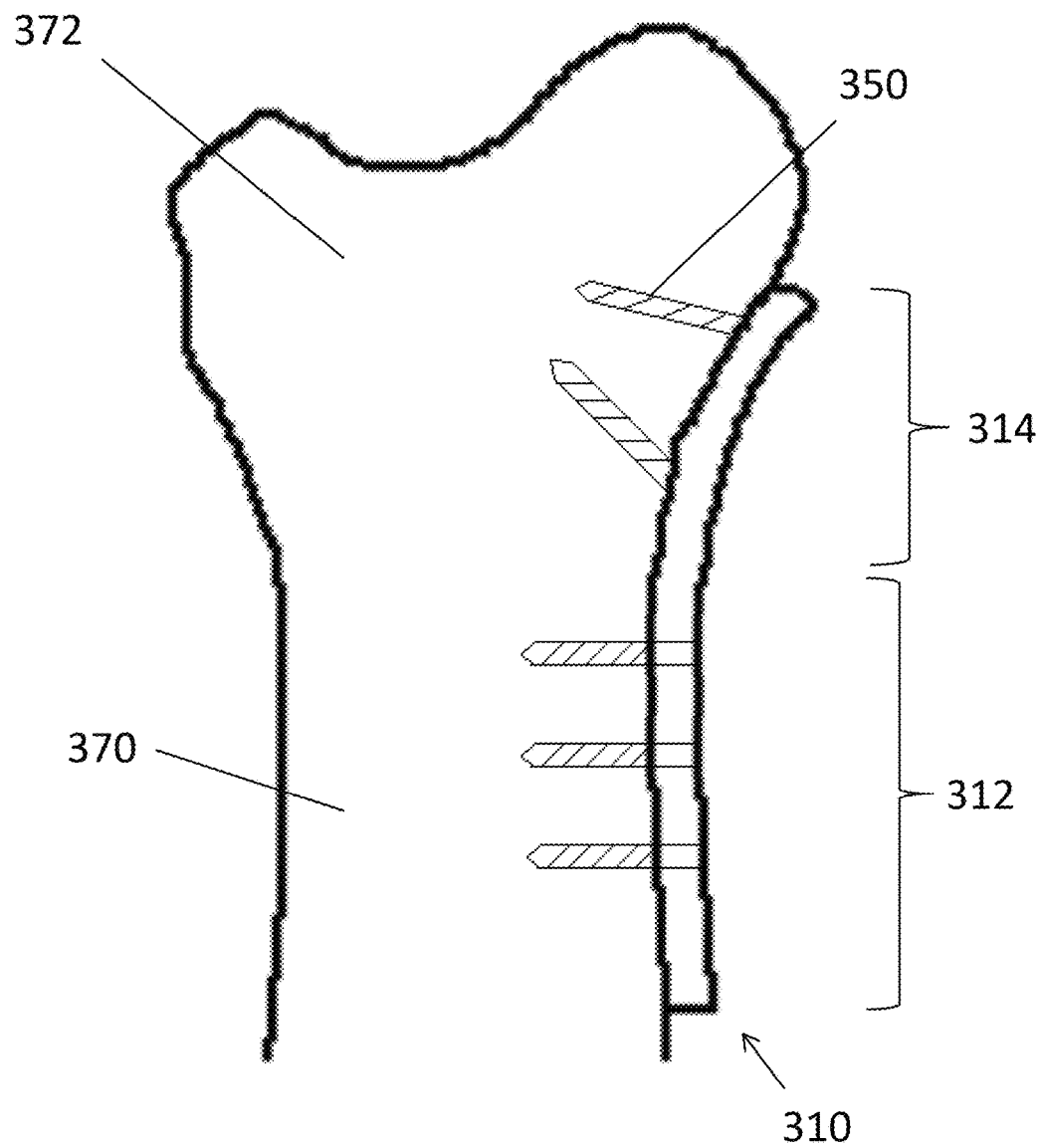
FIG. 8C is a highly schematic view of the bone plate of FIG. 8B implanted onto the humerus of FIG. 8A.

As shown in FIG. 8C, the bone plate 310 may be attached to the humerus 370 with a plurality of fasteners. Although the fasteners are shown as bones screws 350, one or more of the fasteners may take the form of a bone pin, which may be unthreaded with a relatively blunt tip. Generally, the bone screws 350 in coupling the shaft 312 of the bone plate 310 to the shaft of the humerus 370 may be generally parallel to one another and orthogonal to the bone. The bone screws 350 coupling the head 314 of the bone plate 310 to the head 372 of the humerus 372 may be nonparallel relative to one another. The position and orientation of the fasteners in the connected the head 314 of the bone plate 310 to the head 372 of the humerus 370 may be indicated by the deformity in the head 372 of the humerus 370. However, the position of one particular bone screw 350 in the head 372 of the humerus 370 may also be dependent on the position of other bone screws 350 in the head 372 of the humerus 370. For example, care must be taken to ensure that a first bone screw 350 in the head 372 of the humerus 370 does not interfere with other bone screw 350 positioned nearby. The screw planning described above may be useful in planning the implantation of bone plate 310 onto humerus 370, as described in greater detail below.

Figure 8D:
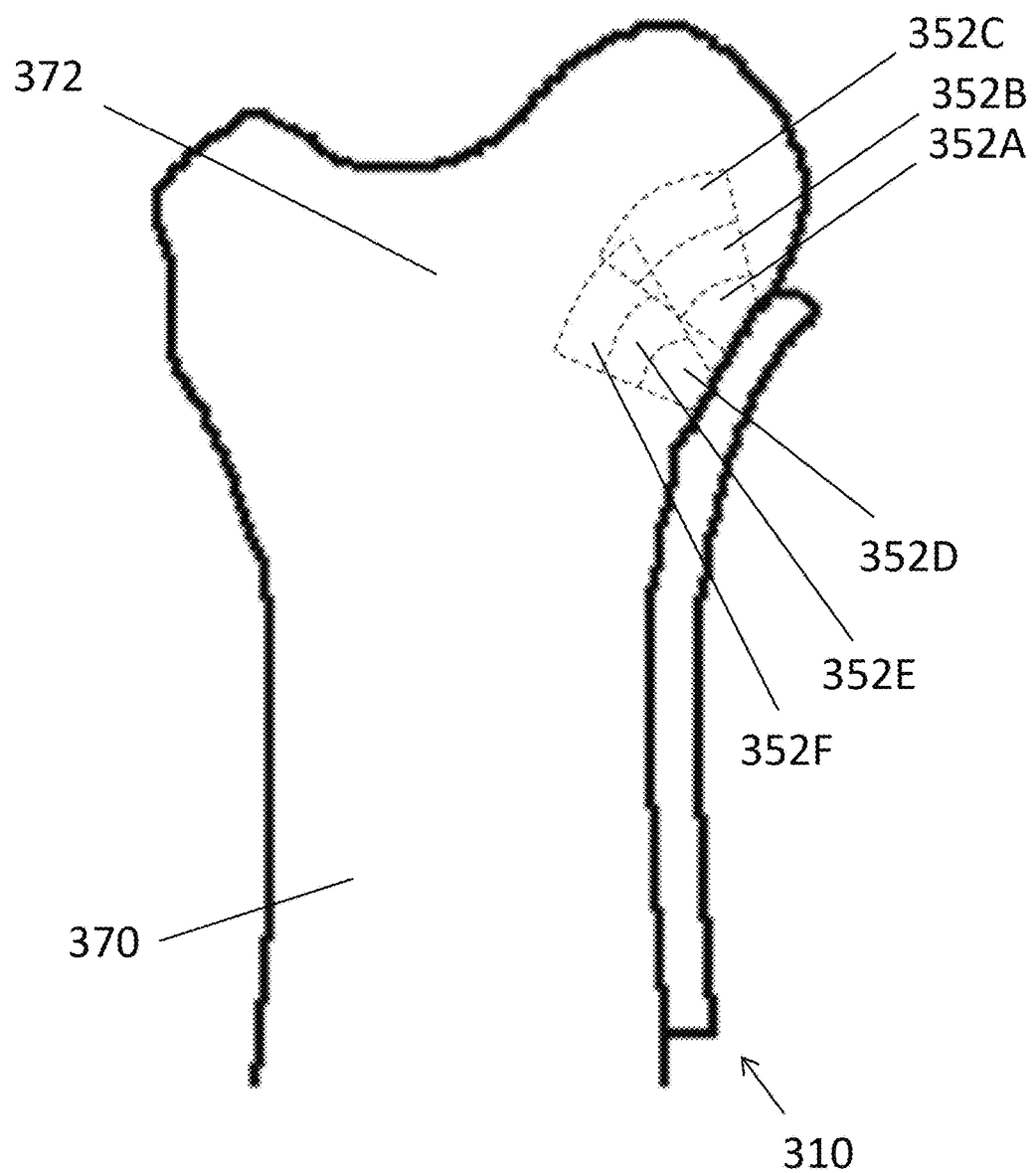
FIG. 8D is a schematic view of the bone plate of FIG. 8B positioned on the humerus of FIG. 8A, with ranges of potential screw volume occupancies illustrated.

Referring to FIG. 8D, a model of a bone plate 310 may be positioned on a model of the humerus 370 in a desired implant position. The model of the bone plate 310 may include volumes 352A-C that a first bone screw 350 may occupy, with the different volumes 352A-C corresponding to different sizes/shapes of the bone screw. Similarly, the model of the bone plate 310 may include volumes 352D-F that a second bone screw 350 may occupy, with the different volumes 352D-F corresponding to different sizes/shapes of the bone screw. The volumes 352A-C and 352D-F may be used in the same or similar manner as described with respect to the tibial implantation procedure described above to ensure that the bone screws 350 are not positioned too close to the edge of the humerus 370, and do not exit the bone.

Figure 8E:
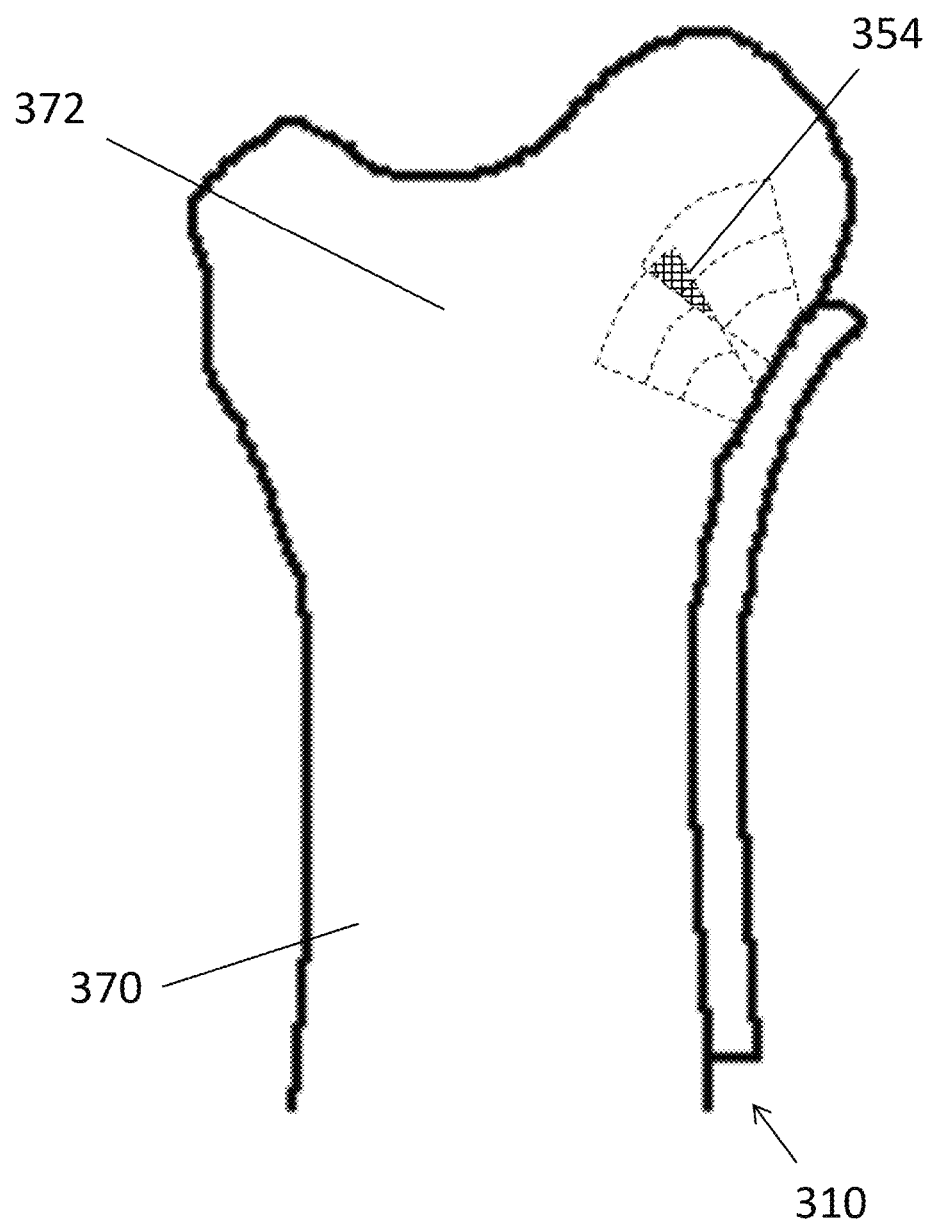
FIG. 8E illustrates volumes of potential screw interference for the system illustrated in FIG. 8D.

In addition to appropriately positioning the bone screws 350 with respect to the anatomy, the screw planning may additionally be used to avoid interference between the bone screws 350. For example, in pre-operative planning similar to that described above in relation to the tibial implantation procedure, the computer displaying the volumes 352A-C and 352D-F may indicate a volume of interference 354. As shown in FIG. 8E, the volume of interference 354, shown as hatched lines, illustrates a volume of overlap between one or more of volumes 352A-C with one or more of volumes 352D-F. Either as part of the pre-operative planning, or during intra-operative navigation utilizing the screw planning, the surgeon may ensure that one or both screws 350 being inserted into the head 372 of humerus 370 avoid the volume of interference 354. In a two screw system, as long as one of the screws 350 does not occupy space of the volume of interference 354, the possibility of those screws contacting one another is eliminated. Similarly, if more than two screws are used with potential interference, it may be preferable for all screws to avoid any indicated volume of interference. Finally, a buffer volume may be added to the volume of interference 354 so to provide a minimum distance between two nearby bone screws 350, as it may be undesirable to have two bone screws 350 very close to one another, even if they do not contact one another. Otherwise, the pre-operative planning and intraoperative navigation using the screw trajectory planning in relation to the tibial implantation described above apply with equal force to the implantation of a bone plate 310 on a bone.

Finally, as noted above, the implant size, shape, position, and/or orientation planning described herein may be used with any implant system in which an implant is being implanted into the body relative to another implant or anatomical structure. As should be clear from the examples described above, the methods described herein may be particularly useful when that bone (or another implant device) provide limitations on the size, shape, position, and/or orientation of the implant device being implanted into the patient. Another example where implant position, size, shape and/or orientation planning may be useful is with acetabular shells of hip implants. For example, an acetabular shell may take the form of a hollow, hemispherical implant with a plurality of apertures therein used to screw the acetabular shell into the acetabulum. The concepts described above may be implemented in a hip implantation procedure to ensure that screws or other fasteners coupling the acetabular shell to the acetabulum are positioned desirably with respect to the existing anatomy. The selection of the number, size, shape, position, and/or orientation of the fasteners may also or alternatively be dependent upon a desired position, sizing, and/or orientation of the acetabular shell. It should be clear that the inventive methods may be applied to other exemplary implant procedures, some of which are briefly described below.

In total knee arthroplasty ("TKA") procedures, a femoral component of a prosthesis system is implanted onto the distal femur. In some cases, whether a primary implant or a revision, the femoral component is anchored to the femur with another component, such as a femoral stem that is coupled to the femoral component and extends into an intramedullary canal created (or already existing from a prior implantation) in the femur. The inventive methods described above may be applied to planning the size, shape, position, and/or orientation of the femoral stem relative to the femur. The size, shape, position, and/or orientation of the stem may include similar limitations as described above in relation to screws being implanted into the tibia during a PKA. For example, it may be desirable to plan the size, shape, position, and/or orientation of the stem component so that a preferred or at least a minimum thickness of bone exists around the circumference or on all sides of the stem. In addition, the planning may take into account the density or other quality of the bone to determine a desired size, shape, position, and/or orientation of the implant within the bone. The methods described above are readily adaptable to planning the size, shape, position and/or orientation of the stem in relation to the femur so that a desired position is obtained, which may include pre-operative and/or intraoperative planning and navigation. In other TKA procedures, particularly in revision procedures, a femoral augment may first be implanted into the femur to facilitate the later implantation of the femoral component and/or its corresponding stem. In these cases, the methods described above may be adapted to planning the size, shape, position, and/or orientation of the femoral augment into the femur. Similarly, in some implant systems, a tibial component may include a stem and/or augment for providing support to the implanted tibial component. The methods described above may be similarly applied to planning the size, shape, position, and/or orientation of augments and/or stems of tibial components of an implant system with respect to the tibial component and/or tibial anatomy. Procedures for implanting femoral components, including corresponding stems and/or augments, are described in greater detail in U.S. Pat. No. 9,011,444 and U.S. Patent Publication No. 2014/0277567, the disclosures of which are both hereby incorporated by reference herein.

Similar to the TKA procedures described above, primary or revision prosthetic hip implantation procedures, in addition to the acetabular shell described above, may include a prosthetic femoral head to articulate with respect to the acetabular shell. Generally, the prosthetic femoral head is attached to a neck or body portion which is attached to a femoral stem extending into an intramedullary canal in the femur to provide support to the prosthetic femoral head in a manner similar to stems used in connection with femoral components of prosthetic knee implant systems. Based on the geometric center of the prosthetic femoral head and/or the existing femoral anatomy, the position, size, shape and/or orientation of the femoral stem may be planned pre-operatively and/or intraoperatively using methods similar to those described above. Some hip implant systems may be modular, with the neck or body portion separately coupled to the femoral stem. With such modular systems, different neck or body portions may be chosen by the surgeon to provide a different offset distance between the geometrical center of the prosthetic femoral head and the longitudinal center of the stem. The particular offset in the prosthetic hip system chosen may be an additional or alternative basis for planning the size, shape, position, and orientation of the stem in the femur.

Another type of procedure that may benefit from the use of the methods described above is an osteotomy, such as a high tibial osteotomy ("HTO"). Generally, in an HTO procedure, one or more cuts are made in the tibia, in the vicinity proximal (or below) the proximal end of the tibia. The cuts may be performed to shorten or lengthen a portion of the tibia. For example, if a patient has arthritis on the lateral portion of a knee joint, with the medial knee joint being relatively healthy, an HTO may be performed on the medial side of the tibia, with a wedge of bone being removed, to shift more weight onto the healthy medial knee joint and divert weight from the arthritic medial knee joint. Generally, a wedge of bone may be removed to shorten the side of the tibia with the bone removed (closing wedge osteotomy) or a cut may be made with a wedge of bone (autograft or allograft) or other biocompatible material inserted into the cut to lengthen the side of the tibia with the bone added (opening wedge osteotomy). Following the osteotomy, a bone plate or other fixation device may be coupled to the bone around the osteotomy with screws or other fasteners to facilitate long term healing of the bone. In either case, when fixing the bone plate to the bone following osteotomy, the methods described above may be employed to plan screw size, shape, position, and/or orientation in a similar manner as described in connection with FIGS. 8A-E. In other words, the size, shape, position, and/or orientation of the screws may be planned based on the anatomy and/or the geometry and features of the particular fixation plate. In addition, for opening wedge osteotomies, such as an opening wedge HTO, the size, shape and/or position of the wedge inserted into the osteotomy may be used as an additional factor for planning the size, shape, position, and/or orientation of the screws (or other fasteners) coupling the associated bone plate to the bone. In one example, it may be desirable to insert fasteners through the fixation plate so that they avoid the implanted wedge, preferably with a buffer distance between the implanted wedge and any fasteners fastening the fixation plate to the bone. However, in other examples, it may be desirable to place fasteners through the wedge, with or without the fastener extending into bone. Certain types of osteotomy procedures are described in greater detail in U.S. Pat. No. 8,241,292, the disclosure of which is hereby incorporated by reference herein.

Still other procedures that may employ the inventive concepts described above include spinal implants. For example, in some patients, it is desirable to fuse adjacent vertebrae together. For example, some implant systems include a cage, device, plate or other structure positioned within adjacent vertebral bodies, in the intervertebral space between adjacent vertebral bodies or on an outer surface of the vertebral bodies. At least one screw extending through the implant systems and into a first vertebral body, and with at least one screw extending through the implant systems and into a second vertebral body adjacent the first. With this configuration, each vertebral body on either side of the cage, device or plate, for example, becomes positionally fixed relative to one another. Generally, the cortical shell of the vertebral body is relatively hard compared to the softer cancellous bone inside. One or both of the prosthetic implant and the anatomy of the vertebral bodies, such as two adjacent vertebral bodies on either side of the prosthetic implant, may be taken into account to plan the size, shape, position, and/or orientation of any fasteners, such as screws, coupling the prosthetic implant to the adjacent vertebral bodies. For example, it may be desirable for a certain distance buffer zone to exist between the posterior cortical shell of each vertebral body and any screw or other fastener passing into that vertebral body. Also, similar to embodiments described above, when more than one fastener is used in any particular vertebral body, planning may help ensure that fasteners do not unintentionally contact one another.

Other spinal procedures may also benefit from incorporating the inventive concepts described above into the spinal procedure. For example, another type of spinal fusion procedure, as an alternative or in addition to the type described directly above, includes implanting pedicle screws into the pedicle bone on the posterior spine and through the vertebral body. Generally, one pedicle screw is positioned through the pedicle on each side of the spine, the screws extending anteriorly, for example, into the vertebral body. This is in contrast to the spinal systems described above, in which screws generally extend posteriorly into the vertebral body. The size, shape, position, and/or orientation of the pedicle screws may be planned using methods similar to those described above, for example to facilitate proper placement through bone and to avoid the spinal cord, and further to keep a distance buffer between the screws and the posterior cortical shell of the vertebral body or any other screws positioned within the vertebral body. Still further, once the pedicle screws are implanted in two or more adjacent vertebral bodies, a rigid element such as a rod is placed within posterior head portions of the pedicle screws, effectively coupling two or more pedicle screws in series on one side of the spine, with a similar element such as a rod connecting two or more pedicle screws in series on the other side of the spine. This configuration fuses vertebral bodies coupled together via the rod extending along adjacent pedicle screws passing into the vertebral bodies. In cases in which a particular bend or curvature of the rod is desired, the pedicle screw size, shape, position and/or orientation may be planned to account for the desired rod curvature. For example, because the rod traverses through proximal head portions of adjacent pedicle screws, the curvature of the rod will be determined, at least in part, by the position of the posterior heads of each pedicle screw in the relevant series. To attain a particular rod curvature, the sizes, shapes, positions, and/or orientations of each pedicle screw in a particular series may be planned so that the posterior head of each pedicle screw is in a desired position and orientation to provide the desired curvature of a rod passing through the series of posterior pedicle screw heads.

Although planning of size, shape, position and/or orientation of bone plate fasteners is described in detail above, for example in connection with FIGS. 8A-E, it should also be understood that the planning methods described herein may be particularly effective when coupling a bone plate to a comminuted fracture. Generally, a comminuted fracture is a fracture in which the bone is broken into several pieces. In order to effectively fix the several broken pieces relative to one another with a bone plate or other similar device, precise placement and number of fasteners through the bone plate and into the bone may be required. The planning methods described above may be employed in comminuted fracture fixation with a bone plate to help ensure that the size, shape, position, and/or orientation of fasteners coupling the bone plate to the bone secure the several pieces of bone desirably relative to one another.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of planning a procedure to fasten an implant to a bone comprising:
displaying on a display device a model of the bone;
displaying on the display device a model of the implant;
positioning the model implant on the model bone in a desired implant position;
displaying in a single image on the display device a first boundary area of a first fastener configured to fasten the implant to the bone, wherein the first fastener has a plurality of separately and independently viable positions, the first boundary area simultaneously representing a range of all the plurality of separately and independently viable positions that the first fastener may have with respect to the implant when fastened to the bone.

2. The method of claim 1, wherein the first displayed boundary area has a plurality of area portions such that each area portion simultaneously represents all possible positions of a different sized first fastener.

3. The method of claim 1, further comprising: providing a first fastener size that has a boundary area positioned entirely within the model bone.

4. The method of claim 1, wherein the step of displaying the model bone includes displaying bone quality information on the model bone.

5. The method of claim 4, wherein the bone quality information is bone density.

6. The method of claim 1, further comprising displaying a second boundary area simultaneously representing a second range of all possible positions that a second fastener may have with respect to the implant when fastened to the bone, the second fastener configured to couple the implant to the bone.

7. The method of claim 6, further comprising indicating on the display an overlap area defined by area occupied by both the first and second boundary areas.

8. The method of claim 1, wherein the step of displaying on the display device the first boundary area of the first fastener is performed prior to positioning the implant on the bone.

9. The method of claim 1, wherein the range of all possible positions that the first fastener may have with respect to the implant is determined from (i) a range of possible angulations between the first fastener and an aperture of the implant adapted to receive the first fastener, and (ii) a length of a shaft of the first fastener.

10. A method of planning a procedure to fasten an implant to a bone comprising:
- displaying on a display device a model of the bone;
- displaying on the display device a model of the implant having at least one aperture for receiving a fastener;
- positioning the model implant on the model bone in a desired implant position;
- displaying in a single image on the display device a first boundary area of a first fastener configured to fasten the implant to the bone, wherein the first fastener has a plurality of separately and independently viable positions, the first boundary area simultaneously representing a range of all the plurality of separately and independently viable positions that the first fastener may have when fully received within the at least one aperture.

11. The method of claim 10, wherein the displayed first boundary area has a plurality of area portions such that each area portion simultaneously represents all possible positions of a different sized first fastener.

12. The method of claim 10, further comprising: providing a first fastener size that has a boundary area positioned entirely within the model bone.

13. The method of claim 10, wherein the step of displaying the model bone includes displaying bone quality information on the model bone.

14. The method of claim 13, wherein the bone quality information is bone density.

15. The method of claim 10, further comprising: displaying a second boundary area simultaneously representing a second range of all possible positions that a second fastener may have when the second fastener is fully received within a second aperture of the implant, the second fastener configured to couple the implant to the bone.

16. The method of claim 15, further comprising: indicating on the display an overlap area defined by area occupied by both the first and second boundary areas.

17. The method of claim 10, wherein the implant is a tibial implant.

18. The method of claim 10, wherein the implant is a bone plate.

19. The method of claim 10, wherein the step of displaying on the display device the first boundary area of the first fastener is performed prior to positioning the implant on the bone.

20. A computer system including a memory and at least one processor configured to execute instructions stored in the memory to: display a model of a bone on a display device;
- display a model of an implant on the display device;
- change a position of the model implant on the model bone to a desired implant position in response to user input;
- display in a single image on the display device a first boundary area of a first fastener configured to fasten the implant to the bone, wherein the first fastener has a plurality of separately and independently viable positions, the first boundary area simultaneously representing a range of all the plurality of separately and independently viable positions that the first fastener may have with respect to the implant when fastened to the bone.

* * * * *